United States Patent [19]

Little

[11] Patent Number: 4,638,102
[45] Date of Patent: Jan. 20, 1987

[54] RECRYSTALLIZATION OF BISPHENOL A BY AZEOTROPICALLY DRYING THE SOLVENT

[75] Inventor: Douglas J. Little, Wichita, Kans.

[73] Assignee: The Dow Chemical Company, Midland, Mich.

[21] Appl. No.: 814,814

[22] Filed: Dec. 30, 1985

[51] Int. Cl.$^4$ ............... C07C 37/84; C07C 37/68
[52] U.S. Cl. ............................................ 568/724
[58] Field of Search ................................. 568/724

[56] References Cited

U.S. PATENT DOCUMENTS

| | | | |
|---|---|---|---|
| 2,791,616 | 5/1957 | Luten, Jr. | 568/724 |
| 3,207,795 | 9/1965 | Prahl et al. | 568/724 |
| 3,326,986 | 6/1967 | Dugan et al. | 568/724 |
| 4,156,098 | 5/1979 | Li | 568/724 |
| 4,242,527 | 12/1980 | Mark | 568/724 |
| 4,294,993 | 10/1981 | Li | 568/724 |
| 4,354,046 | 10/1982 | Ladewig et al. | 568/724 |

*Primary Examiner*—Werren B. Lone
*Attorney, Agent, or Firm*—A. Cooper Ancona; Donald Gunn

[57] ABSTRACT

This invention discloses a high yield azeotropic separation procedure for isomers of bisphenol A. Specifically, the o,p'-isomer is separated from the p,p'-isomer by removal of a cosolvent thus producing crystallization. Water and an organic solvent not miscible with water are used as cosolvents.

18 Claims, No Drawings

RECRYSTALLIZATION OF BISPHENOL A BY AZEOTROPICALLY DRYING THE SOLVENT

BACKGROUND OF THE DISCLOSURE

Bisphenol A is an important commercial intermediate in the manufacture of epoxy, polycarbonate, phenyoxy, polysulfone, and certain polyester resins. It is also used in flame retardants and rubber chemicals. A derivation of bisphenol A is possible by a condensation reaction of phenol and acetone catalyzed by HCl at 150° F.

The p,p'-isomer of bisphenol is commercially favored over the o,p'-isomer and for that reason separation of these two isomers is appropriate. Commercial market expectations of lower o,p'-isomer concentrations have required need of better separation procedures. Current bisphenol A purification processes include crystallization from a solution of wet bisphenol in toluene as disclosed in U.S. Pat. No. 4,354,046; adductive crystallization with phenol as shown in U.S. Pat. Nos. 4,156,098 and 2,791,616; solvent leaching of solid bisphenol as in U.S. Pat. Nos. 3,493,622 and 3,207,795; recrystallization by cooling of a water-wet melt disclosed in U.S. Pat. No. 3,326,986; recrystallization by cooling of a solution in various organic solvents as in U.S. Pat. No. 4,242,527; and recrystallization by adding cosolvents to a solution of bisphenol in an organic solvent as disclosed in U.S. Pat. Nos. 3,919,330 and 4,192,955.

This invention discloses a novel and unobvious separation technique which utilizes a different principle from the above procedures: crystallization of bisphenol A isomers through removal of a cosolvent by azeotropic distillation. The solubility of p,p'-bisphenol in toluene at temperature as high as 98° C. is only 8.6% by weight. With water present at an amount equal to 10% of the weight of bisphenol, formation of a stable liquid solution containing equal quantities of bisphenol and toluene to temperatures as low as 80° C. is possible. This phenomenon is likely due to a synergistic solvent effect related to the depression of the bisphenol freezing point by a small amount of water: 10% water in o,p'-bisphenol will depress its freezing point from 108° C. to 70° C., and 17% water in p,p'-bisphenol will depress its freezing point from 157° C. to 90° C. This data on the solubility of bisphenol in water and toluene, separately and together, sparked curiosity concerning the behavior of a bisphenol/water/toluene solution as the water is removed by azeotropic distillation. This invention is the result of investigating that curiosity; a high yield one step separation technique by azeotropic distillation of the primary isomers of bisphenol A.

DETAILED DESCRIPTION OF THE INVENTION

The two primary isomers of bisphenol A are separated by means of a novel and unobvious crystallization technique. The bisphenol A is dissolved by heating in a mixture of water and toluene. The p,p'-isomer preferentially crystallizes out as the water is removed by boiling as the azeotrope. The toluene layer of the condensed vapors may be, but not necessarily, refluxed to the crystallization vessel.

Crystallization is conventionally carried out by cooling a saturated solution, evaporating the major solvent, or changing the nature of a solvent by addition of a cosolvent. By way of distinction, this invention crystallizes by removal of a cosolvent. The major advantages for the disclosed process of this patentable invention are better separation of p,p'-isomer from the unwanted o,p'-isomer and a larger product yield. This invention is used to produce high quality p,p'-isomer bisphenol from bisphenol A by removal of o,p'-isomer bisphenol and other impurities. The previous best purity obtained in a single-step laboratory procedure with a feed containing about 3% o,p'-isomer bisphenol was 0.09% o,p'-isomer in the product. The process of this invention has produced 0.047% o,p'-isomer content material with certain larger crystals containing only 0.046% o,p'-isomer and yield comparable to a cooling type crystallization. Another use to which this process has been put is in producing a product rich in o,p'-isomer bisphenol by separation of the remaining mother liquor after initial crystallization further cooling and then evaporation of the remaining solvent from the mother liquor. One important step in this invention is the crystallization itself. The solute bisphenol is caused to crystallize by removal of the relatively small proportion of water in the bisphenol/solvent/water mixture. At atmospheric pressure the water boils off in the range of 85°–105° C. The mass of water most preferably should be 10-20% of the mass of bisphenol A used; less water limits the amount of bisphenol A dissolved and more water causes unnecessary expenditure of energy to evaporate it.

There are two proposed explanations for the improved effectiveness of this technique over previous techniques. The first deals with the improvement of solvent selectivity with increasing temperature. Table I shows the change in solubility of both pure isomers with temperature. This drying type crystallization allows precipitation of p,p'-isomer bisphenol at a higher temperature than does a cooling type crystallization of past techniques.

TABLE I

| Solubility of o,p' and p,p'-Isomers of Bisphenol A in Toluene at Various Temperatures | | | |
|---|---|---|---|
| Temp °C. | o,p' gm/100 gm | p,p' gm/100 gm | Selectivity o,p'/p,p' |
| 25 | 4.38 | 0.39 | 11.2 |
| 45 | 14.11 | 0.847 | 16.6 |
| 64 | 55.30 | 2.040 | 27.1 |

The second proposed explanation for the improved effectiveness of this technique over previous techniques relates to the proportion of water present during crystallization. Previous research had concluded that decreasing the amount of water present improves the effectiveness of a cooling-type crystallization from toluene. This drying-type crystallization allows separation of the isomers in the presence of a smaller concentration of water than a cooling-type crystallization. An observable effect of this difference in water content is in the phase behavior of the crystallizer contents. In this cooling type crystallization, two nearly equal volume liquid phases form: a toluene rich upper phase and a wet bisphenol rich lower phase. Upon cooling, crystals form in the wet bisphenol rich phase. Upon heating and subsequent removal of water, the bisphenol is transferred into the toluene rich phase leaving only a very small amount of water which is removed as vaporization proceeds. The crystals actually form out of a toluene solution due to the influence of increasing temperature and decreasing water content.

Although toluene is used as the solvent in the examples of this disclosure, other organic solvents not miscible with water can be used. Various solvents can be suitable replacements for toluene such as chloroform, benzene, xylene, ortho-dichlorobenzene, ethylene dichloride, 1,1,1-trichloroethane, and methylene chloride. Solvent to bisphenol A ratios of 1 to 1 through 3 to 1 all worked equally well, but the preferred ratio is 2 to 1. Lower ratios would work also, but at some point, purity would be compromised. Higher ratios might produce slightly better product purity at the cost of overall yield.

Pressure limits are not precisely fixed. The lower limit would be expected at the point where boiling would be lowered to temperatures into the range of 68°–72° C. and solid bisphenol would be crystallized out by cooling. Upper pressure limits would normally be expected to beat the temperature required to boil off the solvent/water azeotrope exceeds 157° C., the melting point of the p,p'-isomer of bisphenol. The azeotropic evaporation rate used in this invention is such that the water is removed in 2-3 hours. Excessive boiling rates would be expected to decrease product purity.

By the method of this invention, a high purity p,p'-isomer of bisphenol may be crystallized by azeotropically drying a concentrated wet bisphenol A/toluene solution. Using this novel and unobvious method, a product with reduced content of o,p'-isomer of bisphenol can be produced compared with other known single-stage methods of purification. Another beneficial aspect of the technique of this invention is the observed ability to produce larger crystals than previously used techniques. This enables production of a crystalline product with superior handling characteristics due to the ease of handling large crystals which flow over themselves readily. These larger crystals contain even higher purity p,p'-isomer bisphenol due to lower content of o,p'-isomer bisphenol. This is probably due to the large crystals longer life, that is, the largest crystals are formed first so that their growth began from a mother liquor containing a smaller concentration of the o,p'-isomer. Table II reveals crystal size distributions for various crystallization procedures.

TABLE II

| | Crystal Size Distributions for Various Crystallization Procedures | | | |
|---|---|---|---|---|
| Solvent: | Water | Toluene | Water | Toluene |
| Procedure: | Batch | Batch | Continuous | Continuous |
| Crystallization: | Cooling | Drying | Cooling | Cooling |
| Sieve (max opening) | | | | |
| 14 (1.4 mm) | 0.3% | 41.3% | 18.6% | 94.4% |
| 30 (0.6 mm) | 4.8 | 38.5 | 34.4 | 5.2 |
| 50 (0.3 mm) | 38.9 | 9.5 | 36.9 | 0.2 |
| 100 (0.15 mm) | 48.7 | 4.9 | 5.5 | 0.1 |
| 140 (0.106 mm) | 6.1 | 5.3 | 4.0 | 0.1 |
| 200 (0.075 mm) | 0.8 | 0.5 | 0.6 | nil |
| PAN (0) | 0.3 | nil | nil | nil |

Crystal size is reported as the percent of the total sample weight which is retained on each sieve.

The temperature at which the isomer crystals form is higher in this drying type crystallization than in a conventional cooling type crystallization. Separation of the crystals from their mother liquor before allowing the suspension to cool significantly is essential to maintaining high product purity as additional material of lower quality will crystallize out of the mother liquor upon cooling.

The following examples are illustrations of specific embodiments of the invention.

EXAMPLE 1

In a flask, 400 gm of bisphenol A containing 3.1% of o,p'-isomer was mixed with 40 gm of water and 950 gm of toluene, and was heated with agitation to 102° C. The vapor generated by the mixture was removed from the flask and condensed. The mixture was cooled to 75° C. and the resulting solids were separated by vacuum filtration. Remaining mother liquor was removed by washing the resulting solids with 200 gm of toluene at room temperature. The washed solids were then dried and analyzed; they weighed 332.1 gm and contained 0.062% o,p'-isomer. Final yield of p,p'-isomer bisphenol to initial feed was 86.4%. The mother liquor from the initial mixture was allowed to cool slowly to 25° C., then the remaining liquid was decanted off of the solids formed during this cooling. These secondary recovered solids contained 1.6% o,p'-isomer and the liquid contained 1.5 times as much o,p'-isomer as p,p'-isomer. In addition, the secondary solids recovered by further cooling of the mother liquor, representing 10.5% of the p,p'-isomer in the feed, are suitable for recycle. Using this technique, the solids formed crystals which were of relatively large size, with 45% failing to pass through 0.2 mm mesh.

EXAMPLE 2

In order to test the selectivity of dry toluene for the separation of o,p'-isomer bisphenol from p,p'-isomer bisphenol, the following procedure was used. Specifically, a determination was made of the maximum o,p'-isomer ratio attainable in the mother liquor. A 1000 ml 3-neck spherical flask was equipped with an air driven stirring motor with a paddle agitator, a thermometer to measure the temperatures of both the liquid and the vapor phases, and a distillation condenser to remove condensables in the vapor phase rather than refluxing them. 151 gm of bisphenol A containing 3.06% o,p'-isomer, 151 gm of toluene, and 21 gm of deionized water were charged to the flask and heated to 98° C. followed by cooling to 80° C. The resulting mother liquor was removed using a fitted glass filter on the end of glass tube connected to a vacuum. 140 gm of toluene was added and agitated in order to wash the resulting solids. The mixture was then vacuum filtered and the solids dried under vacuum. The removed mother liquor was allowed to cool slowly to room temperature, then the liquid was decanted off the solid material that was formed during cooling.

It is observed that upon heating the bisphenol A was melted by 80°–82° C. At 85° C. vapor started to flow to the condenser producing a distillate containing two liquid phases. This mixture distilled off in the range of 85°–86° C. No additional vapor was observed until the temperature reached 95.5° C. whereupon more two phase distillate was taken overhead between 95.5°–96.5° C. Crystals appeared quickly during this time. Heating was continued to 98° C. with no more vapor observed. The crystal slurry was cooled to 80° C. before removal of the mother liquor. The cooled mother liquor contained 4.2% p,p'-isomer bisphenol and 7.4% o,p'-isomer bisphenol. The total mass of crystalline solids recovered, excluding those precipitated from the cooling mother liquor, was 129.1 gm for a yield of 88% based on initial feed of bisphenol A.

EXAMPLE 3

To further test the selectivity of dry toluene for the separation of o,p'-isomer bisphenol from p,p'-isomer bisphenol, the procedure of Example 2 was repeated.

150 gm of bisphenol A, containing 3.06% o,p'-isomer, 510 gm toluene, and 15 gm of deionized water were heated with stirring to 105° C. The resulting mixture was cooled to 91° C. and vacuum filtered. A 78 gm sample of wet crystals was washed with 234 gm of toluene by agitating for 10 minutes at room temperature. The crystals were then vacuum filtered and dried overnight in a nitrogen purged vacuum oven. This sample contained 877.2 ppm of o,p'-isomer bisphenol in 67.7 gm of dried crystals. The mother liquor was allowed to cool overnight at room temperature and then the mother liquor liquid was removed from the further crystallized solids. The mother liquor liquid contained 0.81% o,p'-isomer bisphenol and 0.76% p,p'-isomer bisphenol while the mother liquor solids contained 0.77% o,p'-isomer bisphenol and 25.97% p,p'-isomer bisphenol.

Temperature inflictions were somewhat less distinct than during example 2. Vapor was observed between 85° C. and 101° C. No additional vapor was observed in the range of 101°-105° C.

EXAMPLE 4

To further test the selectivity of dry toluene for the separation of o,p'-isomer bisphenol from p,p'-isomer bisphenol, the procedure of Example 2 was repeated.

400 gm of bisphenol A containing 30.6% o,p'-isomer, 40.2 gm deionized water and 933 gm toluene were heated together to 103° C. while removing the condensed vapors. The mixture was then cooled to 75° C. and vacuum filtered.

The ratio of wash solvent to bisphenol crystals was decreased from 3/1 ratio of Example 2 to 0.5/1. 342.9 gm of crystals was collected and tested. The crystals contained 860 ppm o,p'-isomer. A yield of 90.9% p,p'-isomer was produced based upon initial feed of bisphenol A. Certain large crystals, about 1 cm long, were isolated and analyzed separately revealing only 580 ppm o,p'-isomer concentration.

The mother liquor was allowed to cool overnight at room temperature and then the mother liquor liquid was removed from the further crystallized solids. The mother liquor liquid contained 1.45% o,p'-isomer bisphenol and 0.69% p,p'-isomer bisphenol.

Boiling of the toluene/water azeotrope started at 85° C. and continued throughout the range of 85°-104° C. A record of distillate volume collected as a function of liquid temperature for this example is shown in Table III. The volume fraction of the collected distillate aqueous phase was constant at 16% over the entire temperature range. The appearance of the crystallizing mixture changes significantly at about 91° C., from two nearly equal volume liquid phases to a large, clear organic phase with very small amounts of clear water in the bottom. The first crystal nuclei were observed at 93.4° C., but the crystal population was very small until the temperature reached 96° C. and then large numbers of crystals were formed.

TABLE III

| Volume of Distillate Collected Recorded As a Function of Liquid Temperature | | | | | |
|---|---|---|---|---|---|
| Temp °C. | Distillate Vol, ml | Temp °C. | Distillate Vol, ml | Temp °C. | Distillate Vol, ml |
| 85.8 | 0 | 89.5 | 99 | *95.0 | 178 |
| 86.6 | 39 | 91.0 | 113 | 95.8 | 197 |
| 87.4 | 56 | 91.8 | 119 | 97.0 | 203 |
| 87.8 | 65 | 92.2 | 121 | 98.2 | 205 |
| 88.0 | 69 | 92.8 | 128 | 99.8 | 208 |
| 88.2 | 78 | 93.4 | 134 | 100.4 | 214 |
| 88.6 | 81 | 94.6 | 135 | 101.4 | 215 |
| 89.0 | 85 | 95.6 | 145 | | |

*The temperature was over-run slightly at 95° C.; lowering heat input lowered the pot temperature from 95.6° C. to 95.0° C., whereby the mixture boiled at constant temperature for about 25 ml. Due to the presence of large crystals in the product, a sieve analysis was performed on a 56.6 gm sample with the results in Table IV.

TABLE IV

| Sieve Analysis on a 56.6 gm Sample of Crystals | | | |
|---|---|---|---|
| Sieve (mesh) | gm | % | Maximum Opening (mm) |
| 6 | 4.4 | 7.7 | 3350 |
| 20 | 16.9 | 29.9 | 850 |
| 70 | 19.4 | 34.3 | 212 |
| 325 | 14.8 | 26.2 | 45 |
| PAN | 1.1 | 1.9 | 0 |

EXAMPLE 5

To illustrate the high o,p'-isomer bisphenol concentration in the mother liquor after initial crystallization of predominantly p,p'-isomer bisphenol, the procedures of Example 2 were utilized here.

5000 lbs. of bisphenol A containing 2.6% o,p'-isomer, 5000 lbs of toluene, and 500 lbs of water were mixed. The mixture was heated to 105° C. to crystallize the predominate p,p'-isomer material, then cooled to 31° C. The mother liquor was separated and then evaporated to recover solids containing 43% o,p'-isomer and 17.4% p,p'-isomer.

EXAMPLE 6

To illustrate the continuous operation of this invention, bisphenol A containing 2.66% o,p'-isomer was utilized in a feed containing a bisphenol A/toluene/water ratio of 1/2/0.1. This mixture was fed continuously at a volume flow rate equal to one half the crystallizer volume per hour for six hours. The feed tank was maintained at 86° C. and the crystallizer at 104° C. At the end of the run, the solids were sampled, rinsed with clean toluene, and found to contain 475 pm of o,p'-isomer bisphenol.

While the foregoing is directed to a preferred embodiment of the present invention, other and further embodiments of the invention may be devised without departing from the basic scope thereof, and the scope thereof is determined by the claims which follow.

What is claimed is:

1. The method of separating o,p'isomers of bisphenol A from the p,p'-isomers of bisphenol A comprising the steps of:
    (a) mixing said isomeric mixture of bisphenol A with water ($H_2O$) and an organic solvent (not miscible in water) for said bisphenol at between about 85° and about 105° C. in the presence of water;
    (b) slowly heating the resulting mixture with agitation to between about 68° C. and the melting point of bisphenol A under a pressure sufficient to vaporize only an azeotropic ratio of water and the organic solvent at the temperature employed;

(c) removing the azeotropic vapors which form from the heated mixture, to reduce the total volume of water in the liquid state of the mixture until crystallization initiates in the liquid at the temperature of the mixture;

(d) cooling the remaining mixture to effectuate first mass of crystalline solids formation in the mixture;

(e) separating the crystalline solids from the mother liquor prior to cooling the mixture to below about 64° C., and recovering a solid product having less o,p'-isomer than in the bisphenol A fed to step (a), and further, optionally subjecting the so recovered solid to at least one of the steps selected from the group consisting of (f) washing the crystalline solids with a solvent; and/or (g) drying the crystalline solids.

2. The method of claim 1 wherein the solvent is any organic solvent which is not miscible with water.

3. The method of claim 1 wherein the solvent is toluene.

4. The method of claim 1 wherein the solvent is one of the group of chloroform, benzene, toluene, xylene, ortho dichlorobenzene, ethylene dichloride, 1,1,1-trichloroethane, and methylene chloride.

5. The method of claim 1 wherein the heating temperature is in the range of about 85° C. to 105° C.

6. The method of claim 1 wherein the mass of $H_2O$ is between about 10% to about 20% of the mass of Bisphenol A.

7. The method of claim 1 wherein the weight ratio of solvent to bisphenol A is between 1/1 and 3/1.

8. The method of claim 1 wherein the weight ratio of solvent to bisphenol A is 2/1.

9. The method of claim 1 wherein the mixture is cooled to at least 75° C. before the solids are separated.

10. The method of claim 1 where the heating rate is adequate to remove the water in the range of 2 to 3 hours.

11. The method of claim 1 further including the steps of to form further crystallized solids;

(a) cooling further the separated mother liquor liquid recovered from the solids;

(b) collecting further crystallized solids from the cooled liquid; and (c) removing these further crystallized solids.

12. The method of claim 11 wherein the liquid is cooled to 25° C. before collecting the further crystallized solids.

13. The method of claim 11 further including the steps of:

(a) separating the mother liquor liquid from any crystallized solids; and (b) evaporating the remaining solvent from the mother liquor to concentrate the o,p'-isomer of bisphenol A within it.

14. The method of separating o,p-isomer of bisphenol A from p,p'-isomer of bisphenol A comprising the steps of:

(a) mixing bisphenol A with water, air, and an organic solvent for said bisphenol not miscible with water from a first temperature to a second and elevated temperature;

(b) heating the mixture with agitation;

(c) removing water vapors from the heated mixture as an azeotrope;

(d) cooling the remaining mixture to form a first mass of crystalline solids in the mother liquor liquid; and (e) removing relatively purified p,p'-isomer of bisphenol A.

15. The method of claim 14 wherein the solvent is one of the group of chloroform benzene, toluene, xylene, ortho dichlorobenzene, ethylene dichloride, 1,1,1-trichloroethane, and methylene chloride.

16. The method of claim 14 wherein the elevated temperature is in the range of about 85° C. to 105° C.

17. The method of claim 14 wherein the $H_2O$ used is between 10% and 20% of the mass of Bisphenol A.

18. The method of claim 14 wherein the weight ratio of solvent to bisphenol A is between 1/1 and 3/1.

* * * * *